US012778401B2

(12) United States Patent
Schütz et al.

(10) Patent No.: US 12,778,401 B2
(45) Date of Patent: Nov. 3, 2026

(54) TIP FOR A SINGLE USE ENDOSCOPE, IN PARTICULAR FOR A SINGLE USE DUODENOSCOPE

(71) Applicant: AMBU A/S, Ballerup (DK)

(72) Inventors: Günter Wilhelm Schütz, Augsburg (DE); Anja Dillinger, Aindling (DE); Kaspar Mat Matthison-Hansen, Helsingør (DK); Felix-Johannes Abicht, Munich (DE); Jonas Hjortlund, Copenhagen (DK)

(73) Assignee: AMBU A/S, Ballerup (DK)

( * ) Notice: Subject to any disclaimer, the term of this patent is extended or adjusted under 35 U.S.C. 154(b) by 684 days.

(21) Appl. No.: 17/922,044

(22) PCT Filed: Apr. 29, 2021

(86) PCT No.: PCT/EP2021/061289
§ 371 (c)(1),
(2) Date: Oct. 28, 2022

(87) PCT Pub. No.: WO2021/219801
PCT Pub. Date: Nov. 4, 2021

(65) Prior Publication Data

US 2023/0165451 A1 Jun. 1, 2023

(30) Foreign Application Priority Data

Apr. 30, 2020 (DE) ..................... 10 2020 111 886.4

(51) Int. Cl.
*A61B 1/07* (2006.01)
*A61B 1/00* (2006.01)
*A61B 1/06* (2006.01)

(52) U.S. Cl.
CPC ............ *A61B 1/07* (2013.01); *A61B 1/00075* (2013.01); *A61B 1/0008* (2013.01); *A61B 1/00091* (2013.01); *A61B 1/0684* (2013.01)

(58) Field of Classification Search
CPC ............ A61B 1/00091; A61B 1/00096; A61B 1/00101; A61B 1/00137; A61B 1/00179;
(Continued)

(56) References Cited

U.S. PATENT DOCUMENTS 4,452,236 A 6/1984 Utsugi
4,573,450 A 3/1986 Arakawa
(Continued)

FOREIGN PATENT DOCUMENTS

CN 107361731 A 11/2017
CN 208017468 U 10/2018
(Continued)

OTHER PUBLICATIONS

German search report in patent application No. 10 2020 111 886.4, dated Apr. 30, 2020, 7 pages, and translation.
(Continued)

*Primary Examiner* — Michael J Carey
*Assistant Examiner* — Stephen Floyd London
(74) *Attorney, Agent, or Firm* — Faegre Drinker Biddle & Reath LLP

(57) ABSTRACT

A tip for a single use endoscope, the endoscope and a method of producing the tip. The tip includes a housing encapsulating a light emitting device and an imaging device in a fluid tight manner, where the light emitting device is arranged on a planar printed circuit board provided within the housing, and the housing at least in part is made from a transparent material and comprises at least one transparent light guiding part or light guiding section for guiding light emitted by the light emitting device to an outside of the tip.

21 Claims, 4 Drawing Sheets

Figure 1:
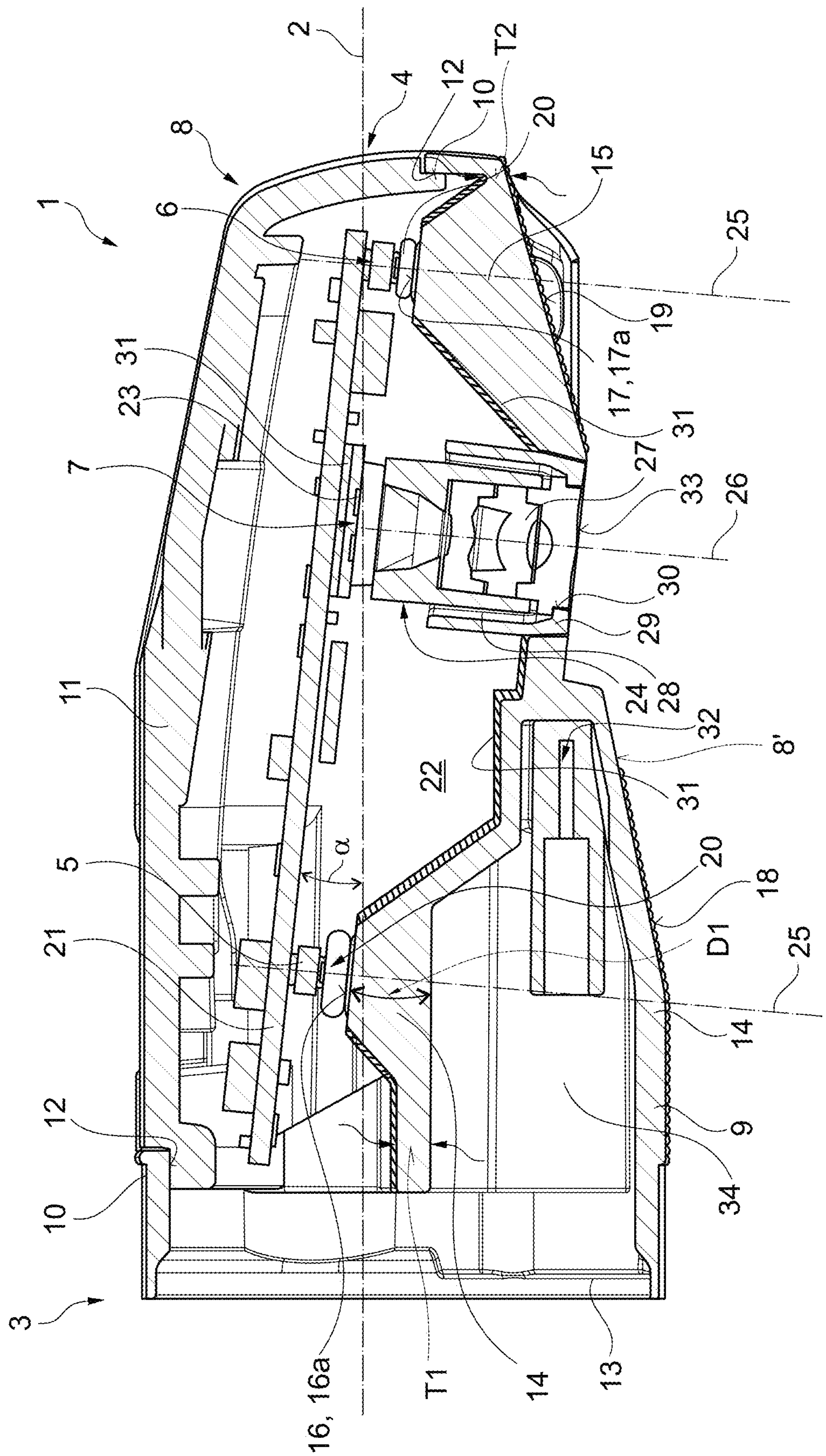

(58) Field of Classification Search
CPC ........... A61B 1/05; A61B 1/051; A61B 1/053; A61B 1/0623; A61B 1/0676; A61B 1/0684; A61B 1/07; A61B 1/0011; A61B 1/00177; A61B 1/0615; G02B 23/2469
See application file for complete search history.

(56) References Cited

U.S. PATENT DOCUMENTS

| | | | | |
|---|---|---|---|---|
| 4,841,949 | A | 6/1989 | Shimizu et al. | |
| 5,201,908 | A | 4/1993 | Jones | |
| 5,323,768 | A | 6/1994 | Saito et al. | |
| 5,562,600 | A | 10/1996 | Matsuno | |
| 5,569,162 | A | 10/1996 | Komi | |
| 5,754,313 | A | 5/1998 | Pelchy et al. | |
| 6,095,970 | A | 8/2000 | Hidaka et al. | |
| 6,315,744 | B1 | 11/2001 | Inaba | |
| 6,824,509 | B2 | 11/2004 | Yamaya et al. | |
| 7,087,010 | B2 | 8/2006 | Ootawara et al. | |
| 7,198,599 | B2 | 4/2007 | Goto et al. | |
| 7,341,555 | B2 | 3/2008 | Ootawara et al. | |
| 7,371,209 | B2 | 5/2008 | Viebach et al. | |
| 7,413,543 | B2 | 8/2008 | Banik et al. | |
| 7,662,094 | B2 | 2/2010 | Iddan | |
| 7,922,650 | B2 | 4/2011 | McWeeney et al. | |
| 7,955,255 | B2 | 6/2011 | Boulais et al. | |
| 8,246,534 | B2 | 8/2012 | Yamaya | |
| 8,313,427 | B2 | 11/2012 | Ishii | |
| 8,485,966 | B2 | 7/2013 | Robertson | |
| 8,986,194 | B2 | 3/2015 | Ohara et al. | |
| 9,554,691 | B2 | 1/2017 | Goldfarb et al. | |
| 9,566,502 | B2 | 2/2017 | Takagishi et al. | |
| 9,655,502 | B2 | 5/2017 | Levy et al. | |
| 9,822,287 | B2 | 11/2017 | Yokoyama et al. | |
| 10,076,438 | B2 | 9/2018 | Bendix et al. | |
| 10,517,470 | B2 | 12/2019 | Hopkins, Jr. | |
| 10,980,558 | B2 | 4/2021 | Ohki | |
| 11,064,866 | B2 | 7/2021 | Yamaya | |
| 2001/0056224 | A1 | 12/2001 | Renner et al. | |
| 2003/0227547 | A1* | 12/2003 | Iddan | A61B 1/051 348/E5.029 |
| 2004/0147807 | A1 | 7/2004 | Viebach et al. | |
| 2005/0222493 | A1 | 10/2005 | Kohno | |
| 2006/0138309 | A1 | 6/2006 | Wimmer | |
| 2007/0016077 | A1 | 1/2007 | Nakaoka et al. | |
| 2007/0249907 | A1* | 10/2007 | Boulais | A61B 1/05 600/179 |
| 2008/0108869 | A1 | 5/2008 | Sanders et al. | |
| 2008/0132760 | A1 | 6/2008 | Takeuchi | |
| 2008/0158349 | A1* | 7/2008 | Miller | A61B 1/00087 348/82 |
| 2008/0300456 | A1 | 12/2008 | Irion et al. | |
| 2009/0043166 | A1* | 2/2009 | Ishii | A61B 1/00179 600/130 |
| 2009/0067067 | A1 | 3/2009 | Yamaya | |
| 2010/0286475 | A1* | 11/2010 | Robertson | A61B 1/00188 600/109 |
| 2011/0288372 | A1* | 11/2011 | Petersen | A61B 1/00096 600/109 |
| 2011/0319717 | A1 | 12/2011 | Pascal | |
| 2013/0172677 | A1 | 7/2013 | Kennedy, II et al. | |
| 2013/0281779 | A1 | 10/2013 | Robertson | |
| 2014/0357948 | A1* | 12/2014 | Kikuchi | G02B 23/2469 600/177 |
| 2015/0005580 | A1 | 1/2015 | Petersen | |
| 2016/0051126 | A1 | 2/2016 | Troller et al. | |
| 2016/0157697 | A1 | 6/2016 | Arai et al. | |
| 2016/0309993 | A1 | 10/2016 | Hosogoe | |
| 2016/0363757 | A1 | 12/2016 | Imai | |
| 2017/0049300 | A1 | 2/2017 | Toyooka | |
| 2017/0078583 | A1 | 3/2017 | Haggerty et al. | |
| 2017/0127915 | A1 | 5/2017 | Viebach et al. | |
| 2017/0202436 | A1 | 7/2017 | Chang | |
| 2017/0215714 | A1* | 8/2017 | Shinji | H04N 23/56 |
| 2017/0245734 | A1 | 8/2017 | Kaneko | |
| 2017/0325671 | A1* | 11/2017 | Hopkins, Jr. | A61B 1/045 |
| 2018/0078121 | A1 | 3/2018 | Yasuda et al. | |
| 2018/0185045 | A1 | 7/2018 | Ohki | |
| 2018/0249895 | A1 | 9/2018 | Calabrese et al. | |
| 2018/0303320 | A1 | 10/2018 | Murayama | |
| 2019/0246886 | A1 | 8/2019 | Harada et al. | |
| 2019/0282070 | A1 | 9/2019 | Vilhelmsen et al. | |
| 2020/0000314 | A1* | 1/2020 | Larouche | A61B 1/00066 |
| 2020/0037860 | A1 | 2/2020 | Yamaya | |
| 2020/0060520 | A1 | 2/2020 | Srensen et al. | |
| 2021/0169308 | A1 | 6/2021 | Fukuzawa et al. | |
| 2021/0290041 | A1* | 9/2021 | Morita | A61B 1/051 |
| 2021/0330175 | A1* | 10/2021 | Kühn | A61B 1/0055 |
| 2021/0338062 | A1* | 11/2021 | Do | G02B 23/2484 |
| 2022/0151480 | A1 | 5/2022 | Hansen et al. | |
| 2023/0112879 | A1* | 4/2023 | Weber | G02B 23/243 600/109 |
| 2023/0277037 | A1 | 9/2023 | Larouche et al. | |

FOREIGN PATENT DOCUMENTS

| | | | |
|---|---|---|---|
| CN | 209951204 | U | 1/2020 |
| DE | 3741938 | A1 | 6/1988 |
| DE | 29613103 | U1 | 10/1997 |
| DE | 19925323 | A1 | 12/2000 |
| DE | 102008026537 | A1 | 3/2009 |
| DE | 102015113020 | A1 | 2/2017 |
| EP | 0591310 | B1 | 4/1997 |
| EP | 1925252 | A1 | 5/2008 |
| EP | 1421894 | B2 | 2/2011 |
| EP | 2022389 | B1 | 1/2012 |
| EP | 3153088 | A1 | 4/2017 |
| EP | 3207852 | A1 | 8/2017 |
| EP | 3243426 | A1 | 11/2017 |
| EP | 3403566 | A1 | 11/2018 |
| EP | 3539450 | A1 | 9/2019 |
| EP | 3583884 | A1 | 12/2019 |
| JP | S55-166203 | U | 11/1980 |
| JP | 02-278219 | A | 11/1990 |
| JP | 04-314439 | A | 11/1992 |
| JP | 11-004804 | A | 1/1999 |
| JP | 11-042201 | A | 2/1999 |
| JP | 2000-157486 | A | 6/2000 |
| JP | 2001-212074 | A | 8/2001 |
| JP | 2002-253484 | A | 9/2002 |
| JP | 2003-038416 | A | 2/2003 |
| JP | 2006-239184 | A | 9/2006 |
| JP | 2006-246933 | A | 9/2006 |
| JP | 2013-081525 | A | 5/2013 |
| JP | 2015-029764 | A | 2/2015 |
| JP | 2015-165839 | A | 9/2015 |
| WO | 2004/049921 | A1 | 6/2004 |
| WO | 2015/084442 | A1 | 6/2015 |
| WO | 2015/107801 | A1 | 7/2015 |
| WO | 2017/025435 | A1 | 2/2017 |

OTHER PUBLICATIONS

Frirst examination report in related Danish application No. PA2020 70273, dated Aug. 11, 2020, 9 pages.
Intention to grant related Danish application No. PA2020 70273, dated Apr. 23, 2021, 2 pages.
International Search Report and Written Opinion received for PCT Patent Application No. PCT/EP2021/061001, mailed on Sep. 13, 2021, 12 pages.
International Search Report and Written Opinion received for PCT Patent Application No. PCT/EP2021/061289, mailed on Aug. 5, 2021, 10 pages.
Second examination report in related Danish application No. PA2020 70273, dated Feb. 25, 2021, 4 pages.

* cited by examiner

TIP FOR A SINGLE USE ENDOSCOPE, IN PARTICULAR FOR A SINGLE USE DUODENOSCOPE

CROSS REFERENCE TO RELATED APPLICATIONS

This application is a National Stage entry under 35 U.S.C. § 371 of International Application No. PCT/EP2021/061289, filed Apr. 29, 2021, which claims priority from and the benefit of German Patent Application No. DE 10 2020 111 886.4, filed Apr. 30, 2020; said applications are incorporated by reference herein in their entirety.

DESCRIPTION

The present disclosure refers to a tip or endoscope tip/duodenoscope tip for a single use endoscope, in particular for a single use duodenoscope, the tip comprising at least one light emitting device, an imaging device and a housing encapsulating the at least one light emitting device and the imaging device in a fluid tight manner. Besides, the present disclosure relates to a method for manufacturing a tip for an endoscope.

General Technical Background of the Disclosure

Endoscopes and similar specialized instruments as bronchoscopes, arthroscopes, colonoscopes, laparoscopes and in particular duodenoscopes are well known from the state of the art and are used for visual examination and diagnosis as well as to assist in surgery. A conventional endoscope generally consists of a connector unit for connecting the endoscope with a supply unit for fluids, gas, light and energy, a control handle connected to the connector unit by a connecting hose/tube and an elongated insertion tube/insertion hose, which on its proximal end portion is connected to the control handle and on its distal end portion carries a tip (endoscope tip, duodenoscope tip). In particular in the case of duodenoscopes the tip is an articulating tip, i.e. a tip that can be moved and bend into different directions, and contains several components including illuminating means such as light-emitting diodes or fiber optic light guides connected to a proximal source of light, image capturing means such as a miniature video camera, and an elevator for a working instrument like e.g. a forceps elevator.

At this point, the expressions "distal" and "proximal" are defined for the whole application (including the description of the disclosure) as follows:

Distal: In the direction away from a user (toward the patient)

Proximal: In the direction toward the user (away from the patient)

The sterilization of the insertion hose/tube as well as of the tip is a very critical aspect and contains a number of problems/drawbacks. For example due to sensitive electrical elements as well as optical elements contained in the tip and due to materials used for the tip and the insertion tube there is a limitation regarding sterilization parameters and disinfection means. In particular, such components may not be accomplished in a high temperature and high pressure way and the like. In result, few sterilization means are available, and the problem of incomplete sterilization exists universally. Moreover, a duodenoscope has more complicated functional structures than other endoscope structures, so there exists a higher sterilization risk.

Another problem related to common multi use endoscope tips is that they are very expensive, heavy and require high maintenance. Known tips generally have a rather complex design, as they comprise an opaque housing with openings for light emitted by a light source inside the tip and with an opening for incoming light to be received by the light sensing device or imaging device. Any opening in the housing has to be sealed to protect inner parts/functional elements of the tip as the light emitting device and the imaging device against body fluids and fluids used during sterilization and maintenance. A further drawback is that known endoscope tips are commonly made from metal and have a rather high weight.

Due to the above problems, common endoscope tips are less suited for use in emergency medicine and mobile entities as ambulances, rescue helicopters and life boats.

SUMMARY OF THE DISCLOSURE

Against this background, the object of the present disclosure is to reduce the mentioned disadvantages of the prior art, and in particular to provide a tip as well as a method for manufacturing such tip, in particular an endoscope tip/duodenoscope tip well suited for single use, while avoiding openings in the housing whenever possible.

This object is achieved by a tip according to claim 1, i.e. a tip for/of a single use endoscope, in particular for a single use duodenoscope, the tip comprising at least one light emitting device, an imaging device and a housing (housing shell) at least partly encapsulating the at least one light emitting device and the imaging device preferably in a fluid tight manner, wherein the housing at least in part is made from a light transparent material, in particular a transparent plastic material. Preferably, the entire tip is completely made from the transparent material. A tip within the meaning of the disclosure especially comprises an endoscope tip as well as a duodenoscope tip.

A key issue of the present disclosure is, that the tip is a single use tip for/of a single use endoscope and a single use duodenoscope, respectively. It is therefore very well suited for use in emergency medicine, in particular for use in mobile entities as ambulances, rescue helicopters and life boats, for initial examination of a patient. The tip in particular can provide a low cost single use article, which is lightweight and intended for disposal after use.

The tip according to the disclosure provides a kind of a camera tip for an endoscope as well as for a duodenoscope. The imaging device and the at least one light emitting device are each built in the housing (housing shell) made of a transparent material. Such a material could be any transparent material, however, it is preferred to use a transparent plastic/resin material. Plastic/resin material has a number of advantages for a single use tip, as e.g. low cost, adequate mechanical characteristics as elasticity, low brittleness, a high suitability for manufacturing methods as injection molding and low weight. The light emitted from the at least one light emitting device penetrates through the transparent material of the housing and is sent to the outside, e.g. into a body cavity, from at least a part of the outer surface of the housing.

The housing of the tip preferably is made by injection molding of a transparent plastic material being suitable for medical use like PE, Silicon, PVC, etc. It may therefore be made with a nearly unlimited geometry and required dimensions. Additionally, injection molding is well suited for making a high number of parts with low costs. According to the disclosure, the housing may be monolithically made from the transparent material and provide a one-part-tip. This is advantageous as no sealing is required between distinct parts. However, the housing may be designed as a multi-part housing.

Advantageous embodiments of the disclosure are claimed in the dependent claims and are explained in more detail below.

According to one embodiment the at least one light emitting device may comprise an LED. Such light emitting devices do not require large amounts of energy and provide light of high quality well suited for medical examination and surgery. Additionally, LEDs require only small space and are very robust.

A further embodiment probably claimed separately and independently is characterized in that the at least one light emitting device and/or the imaging device are arranged on and/or connected, in particular electrically connected, to a printed circuit board (PCB). Advantageously, the PCB is oriented essentially parallel (slight inclination is acceptable) to a longitudinal axis of the tip/endoscope tip/duodenoscope tip extending from a distal tip end to a proximal tip end. In particular, the PCB may be oriented in an angle of 4° to 10° to the longitudinal axis, most preferred of 6° to the longitudinal axis wherein the light emitting direction is substantially in radial with respect to the endoscope.

According to a further embodiment probably claimed separately and independently, the at least one light emitting device and the imaging device are arranged on and/or connected, in particular electrically connected, to a common (single) printed circuit board (PCB). This allows for simple and exact mounting of the PCB in the housing during manufacture of the tip. The PCB may be aligned relative to the housing by a direct contact between PCB and bearing structures provided by the housing. Alternatively, the PCB may be aligned relative to the housing by contact of the at least one light emitting device with the housing and/or the imaging device with the housing. This allows a very exact and easy positioning of the light emitting device and the imaging device and therefore a very high optical accuracy of the tip. Further, the light emitting device and the imaging device may be arranged on one common PCB, which is arranged nearly parallel to the longitudinal axis of the tip, thereby providing a cost efficient arrangement, which is less prone to errors and has fewer failures due to solder joints.

A further embodiment probably claimed separately and independently is characterized in that the at least one light emitting device is connected to the housing by/via transparent adhesive or a transparent glue, providing a layer between the light emitting device and the housing/housing shell/casing. This connection preferably is such, that there is no direct contact between the at least one light emitting device and the housing. The transparent adhesive allows the introduction of light emitted by the light emitting device into the transparent material of the housing without any gaps/air there between, while at the same time providing accurate positioning of the PCB and/or the light emitting device and/or the imaging device. Therefore, within the disclosure the transparent adhesive provides a kind of an optical filler/optical guiding material, for guiding light between the light emitting device and the transparent material of the housing.

The housing in particular may comprise light guiding parts or light guiding sections for guiding light emitted by the at least one light emitting device to the outside of the tip. Such light guiding parts/sections preferably are monolithically formed by the transparent material of the housing of the tip. They comprise an inside surface pointing to the inside of the housing and in particular to the at least light emitting device. They further comprise an outside surface pointing to the outside of the tip, i.e. into a body cavity to be examined by using the tip. The space between the inside surface and the outside surface preferably is monolithically filled by the transparent material of the housing. By an alignment of the inside surface and the outside surface relative to the tip, in particular to the longitudinal axis of the tip, the area illuminated by the light emitted from the tip can be accurately defined and aligned with the optical axis of the imaging device. Advantageously, an inside surface of the light guiding part/section of the housing is highly glossy to prevent or avoid transmission losses of light emitted by the at least one light emitting device. Additionally, because a glue layer is preferably provided between the inside surface of the light guiding part/section and the light emitting device a proper light transmission into the housing material is achieved.

Alternatively or additionally, an outside surface of the light guiding part/section of the housing may have a rough surface (different to the surface roughness of the remaining housing part), in particular in order to distribute light exiting the tip from its inside to the outside, i.e. into a patient's body cavity. The roughness $R_A$ of the outside surface of the light guiding part/section may be outside the roughness that is normally achieved by an injection molding process. In particular it may be a roughness $R_A$ of more than 1 μm, preferably with a roughness $R_A$ between 1 μm and 10 μm, more preferred with a roughness $R_A$ of about 2.5 μm. An $R_A$ of 2.5 μm corresponds to a surface roughness of CH28 in the VDI 3400 standard (VDI is the Society of German Engineers). An $R_A$ of 1 μm corresponds to CH20 in the VDI 3400, and an $R_A$ of 10 μm corresponds to CH40. The provision of the desired roughness for example may be achieved by a blasting process, e.g. sand blasting or the like, that is applied to the concerning parts/outer surfaces of the tip housing. The roughness of the outside surface of the light guiding part/section is preferably such that an area within which the position of focus of the imaging device may be located/varied is evenly illuminated.

According to a further embodiment, the imaging device may comprise an imaging chip provided by the printed circuit board or on the PCB and a focusing system, in particular a lens system for providing an image on the imaging chip. The lens system may be in the form of a lens barrel which is preferably mounted on the imaging chip as a lens barrel carrier. It may in particular be an adjustable lens system for varying the position of focus. The optical axis of the lens system is preferably orthogonal to the plane of the PCB and therefore orthogonal to the longitudinal axis of the tip. In particular, the optical axis of the lens system may be oriented in an angle of 4° to 10° to the vertical of the longitudinal axis, most preferred of 6° to the vertical of the longitudinal axis, such that the viewing direction of the tip is a little bit to the backside/to the proximal direction.

A further embodiment probably claimed separately and independently is characterized in that the tip comprises an opaque layer or an opaque potting (preferably filling-up cavities inside the housing). Such layer/potting in particular may be provided for shielding the camera chip and the lens system against disturbing light entering the transparent housing from the LED's and/or from outside. The opaque layer/potting may be provided on the housing, in particular on at least a part of its inside surface. Alternatively, the potting/layer may be provided on the functional elements to be shielded. It needs not to be provided in/on the entire housing, it is sufficient, if it shields the imaging chip and the focusing system, such that these parts of the tip are shielded against and not influenced by disturbing light coming from the outside through the transparent housing into its inside. However, it is within the scope of the disclosure that the complete imager board/the entire PCB with all functional parts thereon is protected/shielded against disturbing light. In particular, it is advantageous, if according to one embodiment probably claimed separately and independently the focusing system/lens system is surrounded by an opaque protective structure e.g. in form of a ring, foil, cover, etc., Such a protective structure may also be made from plastic, preferably by 2K molding with the transparent housing. Further, a space/cavity between the imaging device and the protective structure may be filled/casted with additional opaque potting. Accordingly, a full light protection of the camera chip and the lens system is achieved by blocking light emitting through cavities inside the housing but also by preventing light spreading through the housing material from entering into the lens system especially at the contact area between the lens system and the housing.

Preferably, the axis of light emitted from the endoscope tip is essentially parallel to the optical axis of the imaging device. This results in a better utilization of the available light for image capture and image processing and in less annoying reflections due to misdirected light.

A further embodiment probably claimed separately and independently is characterized in that the endoscope tip further comprises a transparent nozzle device for rinsing the tip, in particular for rinsing an outer surface of the imaging device. Additionally or alternatively, the tip may comprise a transparent nozzle for insufflating a gas and/or air. These functions may also be achieved by one single nozzle having both functionalities. The transparent nozzle device may be attached to the tip by a transparent grout or may be formed integrally with the housing. By using a transparent nozzle material (and a transparent grout if used), formation of shadows and drop shadows can easily and effectively be avoided, which results in high image quality. This allows to locate the nozzle at/in the tip housing independently from/regardless the light transmission path in the housing material exclusively for the purpose to optimize the cleaning result at the lens system. More concrete, the nozzle may be located between an LED and the respective outer light emitting surface part of the housing such that the nozzle substantially represents a part/portion of the light transmission path. In other words, the tip may comprise a nozzle device for rinsing and/or insufflating, the nozzle device being arranged inside/within a cavity of the housing between (at least) two opposing wall surfaces, wherein the cavity comprises a transparent potting in order to enhance guiding light from one wall surface to the opposing wall surface. Preferably, one wall of the two opposing walls is a transparent exterior wall of the housing to an outside of the tip and the other wall is a transparent interior wall or structure that is inside the tip and facing toward and/or receiving light from the at least one light emitting device.

According to a further embodiment probably claimed separately and independently the tip is a monolithic tip. The tip in particular may be monolithically formed from the transparent material in a single injection molding process. Alternatively, the tip may be a multi-part tip, in particular comprising a first housing part and second housing part, which parts are sealed with each other. Preferably, the tip is entirely closed and with the exception of an opening on its proximal side, where the tip is connected to an insertion tube or insertion hose, it does not comprise any other openings or contacting surfaces that need to be sealed.

With other words one can say that the disclosure comprises the use of a single planar PCB for assembly reasons as well as the use of a transparent housing. The housing may be filled with an opaque potting, for example with black glue, so that light travel into the sensor/camera chip from the backside of the PCB or even inside the length direction of the PCB may be avoided or at least reduced. There may be provided a shielding unit for example in form of a black cylinder, cover, foil, etc. around the focusing unit/lens barrel, which shielding unit may serve three purposes:

- first, it ensures a correct mounting/position of the lens barrel,
- second it may prevent (disturbing) light from entering into the lens barrel especially at a contact area between the lens barrel and the housing and
- third it may prevent that opaque potting/black glue exits the housing near or at the focusing unit/lens barrel.

The at least one light emitting device/LED may be fixed to light guides/light transmission paths provided in the housing with a transparent glue, which also may serve as a tolerance buffer. This is advantageous as the height of the lens barrel may vary a lot in order to focus the lens system. Preferably, the at least one light source is not encased within one single monolithic part of the housing.

In summary, it can be said that the disclosure in particular may provide the following advantages:

- the rather expensive and heavy metal body of known tips is replaced with a low cost plastic part
- the tip is very well suited for single use and is intended to be discarded after use
- as there are less openings to be provided in the housing for emitted light as well as for incoming light, there are less problems regarding the sealing of the housing/enclosure/tip compared to known tips
- the mounting and the manufacture of the tip is less cost intensive e.g. due to less parts to be mounted.

The term light guiding part or light guiding section in particular describes a part or a section of a structure, especially a structure of the housing, that has a defined entrance (surface) for the light, a segment/section that is transparent (between entrance and exit) for at least visual light and is adapted in order to pass/guide the light through this section and has an output/exit (surface) where the light leaves the light guiding part or the light guiding section and is emitted to an outside of the tip.

The term planar printed circuit board (PCB) describes a PCB that only extends in one plane. Such flat structure is widely used and particularly simple and cost-effective.

Preferably, the at least one light guiding section of the housing may have a funnel-shaped structure that has, seen in a longitudinal section, a triangular or trapezoidal shape, a narrow entrance surface of the funnel shaped structure facing toward the at least one light emitting device and a wide exit surface facing toward a side surface of the tip. Such structure enhances a light guiding to the outside of the tip. In particular, a light guiding with an expanding cross sectional area may have a collimating effect that is described in EP 3 539 450 A1 and which disclosure is hereby incorporated. Preferably, the light emitting device is glued (via a glue layer) on the narrow entrance via a transparent adhesive in order to enhance transmission and to minimize transmission losses as well as to serve as a tolerance buffer. Preferably, this structure is provided at a side of the tip that directly abuts or adjoins the distal end of the tip. Preferably, the narrow entrance surface is planar and especially parallel to the planar PCB.

According to another aspect of the disclosure, at least one light guiding section of the housing may be in the form of a plateau shaped base having a top surface serving as an entrance surface for the at least one light emitting device, the top surface being raised with regard to a base (surface) and preferably may have on a bottom surface and/or a side surface a light guiding channel that guides the light to the outside of the housing of the tip. Preferably, the top surface is aligned parallel to the PCB. Preferably, the light guiding section in the form of the plateau shaped base is provided inside the housing, preferably at an interior wall.

The object of the disclosure regarding a method for manufacturing is achieved by a method according to claim 14.

According to the present disclosure, the method comprises the steps: inserting, in particular in/along a straight direction, a planar printed circuit board (PCB) having at least one light emitting device arranged thereon and an imaging device, preferably arranged thereon and/or connected thereto, within an at least partly transparent, preferably complete transparent, housing of the tip; preferably connecting and/or attaching the at least one light emitting device to a light guiding section of the housing by a transparent adhesive, preferably by a glue layer; encapsulating the planar printed circuit board, the least one light emitting device and the imaging device in a fluid tight manner in the housing, preferably by fluid tightly connecting a second housing part to a first housing part. The PCB is preferably a common PCB for at least the light emitting device and the imaging device. Such method has the advantage that a production and an assembly is further simplified. Since the at least one, preferably two, light emitting device(s) is/are arranged on the PCB and the PCB is inserted such that the light emitting device is aligned onto a light guiding section of the housing and especially is glued onto an entrance of the light guiding section of the housing, a design and assembly of the tip can be held simple and effective. The housing itself is used for the guiding the light to an outside of the tip. Since the PCB is planar, in particular a straight insertion is made possible. With such method, preferably a tip of an endoscope according to the present disclose can be produced.

Preferably the method further comprises the step of filling opaque potting in a cavity surrounding at least a focusing system of the imaging device, preferably further surrounding a contact area between the at least one light emitting device and/or a light guiding section.

Preferably, the method may further comprise the step of molding, preferably injection molding, the plastic housing of the tip, in particular before the step of inserting the PCB.

SHORT DESCRIPTION OF THE FIGURES

Further features and advantages of the present disclosure result from the following exemplary and non-limiting description of the figures. These are only schematic in nature and only serve to understand the present disclosure. On the other hand, the formulation of the claims are not restricted to the shown embodiments.

Figure 2:
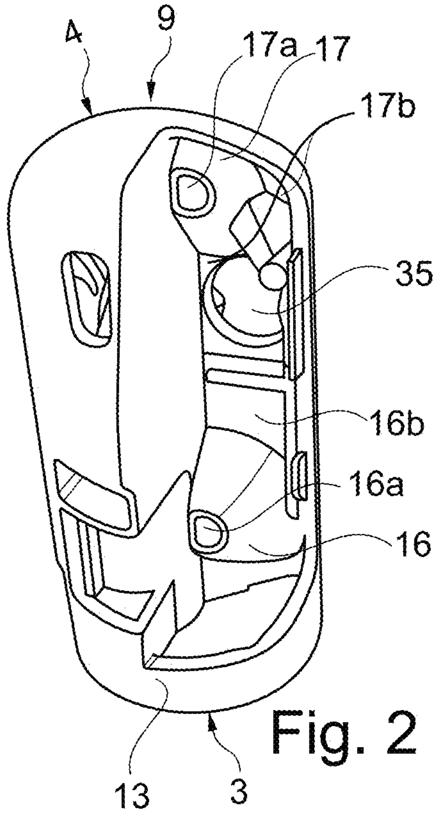
Figure 3:
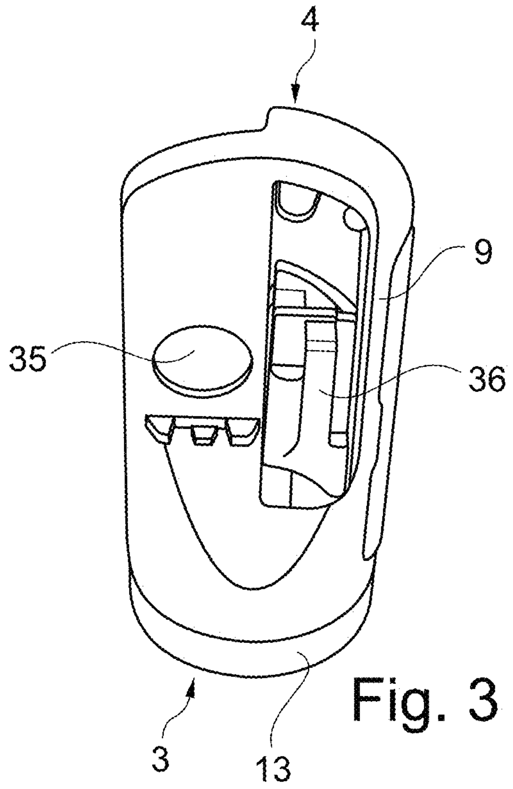
Figure 4:
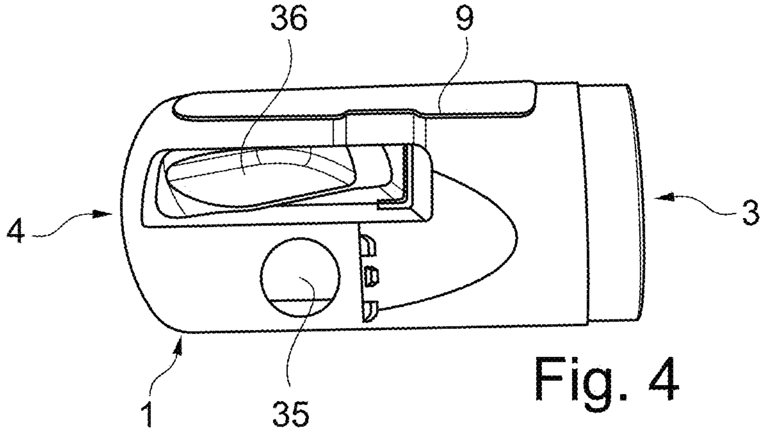
Figure 5:
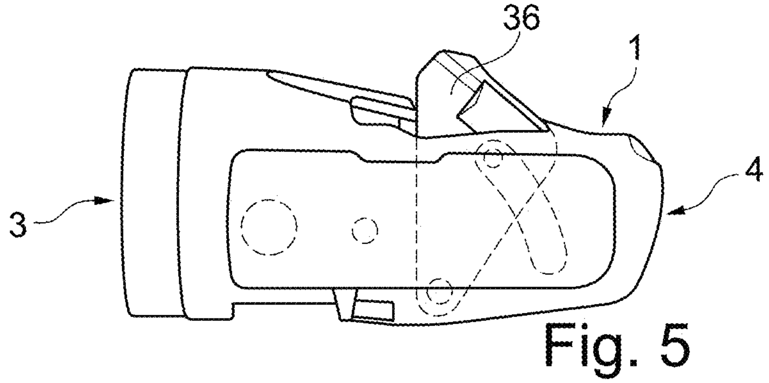
Figure 6:
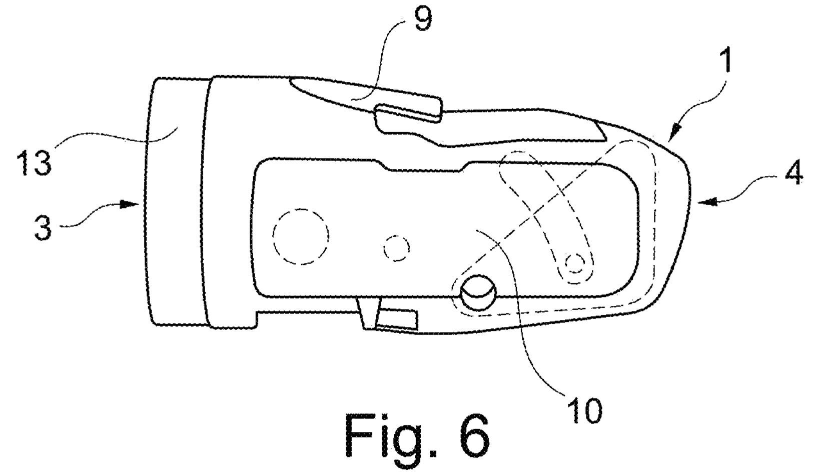
Figure 7:
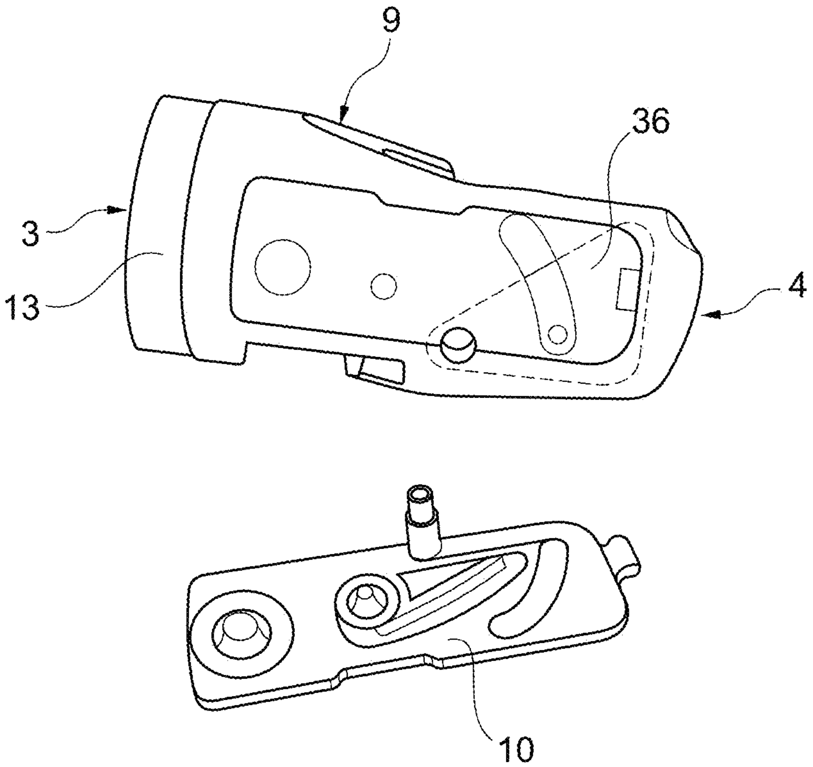
Figure 8:
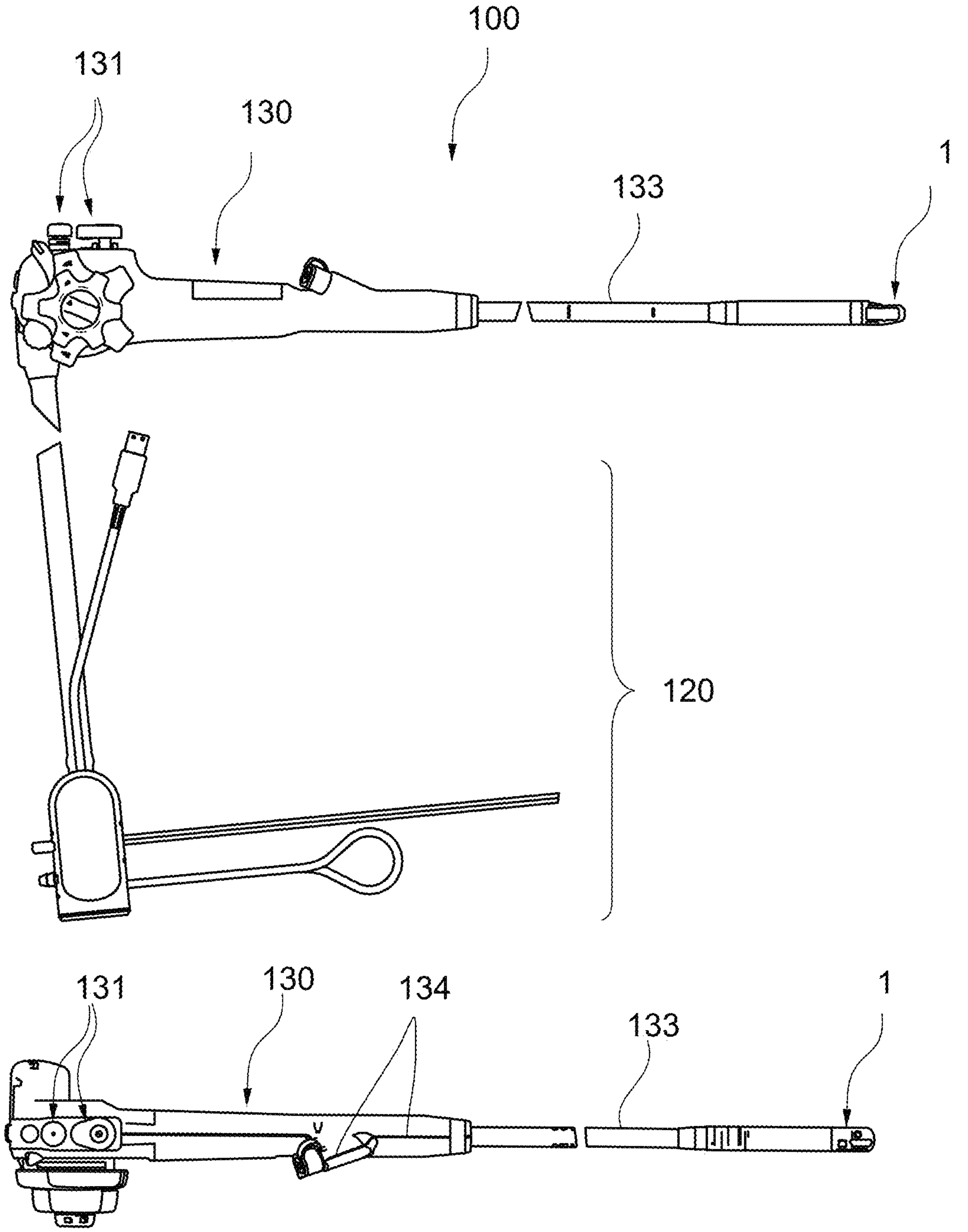

FIG. 1 shows a sectional view of an example of a duodenoscope tip according to the disclosure in the direction of its longitudinal axis, i.e. from its proximal end to its distal end, FIG. 2 shows a perspective view of an example of a duodenoscope tip according to the disclosure form a first viewing direction, FIG. 3 shows a perspective view of the example of a duodenoscope tip of FIG. 2 from a second viewing direction, FIG. 4 shows a perspective view of the example of a duodenoscope tip of FIGS. 2 and 3 from a third viewing direction, FIG. 5 shows a perspective view of the example of a duodenoscope tip of FIGS. 2 to 4 from a fourth viewing direction, FIG. 6 shows a perspective view of the example of a duodenoscope tip of FIGS. 2 to 5 from a fifth viewing direction, FIG. 7 shows a perspective view of the example of a duodenoscope tip of FIGS. 2 to 6 from a sixth viewing direction and FIG. 8 shows an endoscope/duodenoscope according to the present disclosure being adapted to be connected with a supply unit which does not belong to the subject matter of the present disclosure.

DESCRIPTION OF THE PREFERRED EMBODIMENT

To begin with, FIG. 8 shows the endoscope 1 of the present disclosure in its substantially complete structure.

Accordingly, the endoscope 100 is preferably a single use endoscope (duodenoscope) and comprises a connector unit 120 for connecting the endoscope 100 with a (separate) supply unit, which may also be referred to as a base unit, for at least one operating resource (for example, electric power, water, etc.). The endoscope 100 further comprises a supply line located proximal (in the direction toward the user) to/at the connector unit. The supply line is for supplying said at least one operating resource from the connector unit to an endoscope handle 130 which is designed to be held by an user and—in accordance with the manual actuations of several manipulators 131 at the handle 130 by the user—from the handle 130 to a distal (direction away from the user/direction toward the patient) endoscope tip/head 1 (shown in FIG. 1), which is intended to be inserted into a patient's body cavity and which is located at the distal end of an endoscope shaft 133 which shaft 133 is mounted at its proximal end to the handle 130 and into which the supply line is extended. Furthermore, the endoscope shaft 133 comprises at least one so-called working channel 134 extending along the endoscope shaft 133 and having an opening in the tip 1 such that a surgical instrument can be shifted through the working channel 134 to extend beyond the tip 1 into a distal and/or radial direction.

FIG. 1 shows a sectional view of the single use tip 1 for a single use duodenoscope according to FIG. 8. The section is taken along the direction of the longitudinal axis 2 of the tip 1, i.e. from its proximal end 3 to its distal end 4.

The tip 1 comprises at least a first light emitting device 5, a second light emitting device 6, an imaging device 7 and a housing 8 encapsulating the light emitting devices 5, 6 and the imaging device 7 in a fluid tight manner. The housing 8 comprises a first housing part/shell 9 with a first housing seat 10 and a second housing part/shell 11 with a second housing seat 12. The first housing part 9 and the second housing part 11 fit together at their respective housing seats 10, 12 and are sealed (seal is not shown in FIG. 1) along their common contact line at the housing seats 10, 12. On its proximal end 3 the first housing part 9 has an annular connection part 13/connection section 13 for (sealed) mechanical, electrical and/or hydraulic/pneumatic connection with/to the endoscope shaft/endoscopic insertion tube or insertion hose 133 as shown in FIG. 8. A circumferential wall portion 8' extends longitudinally between the distal end 4 and the proximal end 3 of the housing 8. The first light emitting device 5, the second light emitting device 6, and the imaging device 7 face the circumferential wall portion 8', as best seen in FIG. 1. The circumferential wall portion 8' comprises transparent light guiding parts or sections 14, 15 configured to guide light emitted by the light emitting devices 5, 6 to an outside of the tip 1.

The entire first housing part 9 as well as the entire second housing part 11 consist of a light transparent plastic/resin material and are made preferably by injection molding.

The first housing part 9 also comprises a socket-like first light guiding section 14 and a socket-like second light guiding section 15, each for guiding light being emitted by the light emitting devices 5, 6 to the outside of the tip 1. The first light guiding section 14 comprises an (first) inside surface 16 having a light entrance surface 16*a*, while the second light guiding section 15 comprises an (second) inside surface 17 having a light entrance surface 17*a*. Both light entrance surfaces 16*a*, 17*a* preferably are highly glossy to avoid transmission losses of light emitted by the light emitting devices 5, 6. Additionally, the first light guiding section 14 comprises an (first) outside, or light exit, surface 18, while the second light guiding section 15 comprises an (second) outside, or light exit, surface 19. Both outside surfaces 18, 19 are relatively rough compared to other outside surface areas of the housing 8 in order to distribute light exiting the tip 1 from its inside to the outside. The roughness $R_A$ is provided by a sand blasting process and may be more than 1 μm, preferably between 1 μm and 10 μm, more preferred about 2.5 μm. The space/volume between the inside surfaces 16, 17 and the outside surfaces 18, 19 is filled with the transparent material of the housing 8. A distance D1 between a light entrance surface 16*a* of the inside surface 16 and the light exit surface 18 is filled with the plastic material of the housing 8. A distance D2 between a second light entrance surface 17*a* of the inside surface 17 and the outside surface 19 is filled with the plastic material of the housing 8. As shown in FIGS. 1 and 2, portions of the circumferential wall 8' surrounding the light guiding sections 14 and 15, identified as wall portions 16*b*, 17*b*, have thicknesses T1, T2 which are smaller than the distances D1, D2.

The inside surfaces 16, 17 also serve for attachment/contacting of a first LED 5 as first light emitting device 5 and of a second LED 6 as second light emitting device 6. The first LED 5 and the second LED 6 each are attached to light entrance surfaces 16*a*, 17*a*, of the concerning inside surfaces 16, 17 preferably by transparent glue 20. On the side opposite the transparent glue 20 the LEDs 5, 6 are connected to a printed circuit board (PCB) 21, which is located in a cavity 22 provided within the housing 8. Accordingly, the PCB is held by the socket-like light guiding sections 14, 15 via the LED's 5, 6. As is shown in FIG. 1, the PCB 21 is orientated essentially parallel to the longitudinal axis 2 of the tip such that light emitting directions of the LED's are substantially orthogonal to the longitudinal axis 2. In particular, the plane of the PCB 21 is arranged in an angle α of 4° to 10° to the longitudinal axis 2, preferred of 6° to the longitudinal axis 2.

Also arranged on the PCB 21 is the imaging device 7. The imaging device 7 comprises an imaging/camera chip 23 located on and electrically connected to/with the PCB 21 as well as a focusing system 24, in particular a lens system 24 for providing an image on the imaging chip 23. An optical axis 26 of the lens system 24 is, substantially, parallel to the optical axes 25 of light emitted by the LEDs 5, 6. Therefore, also, the imaging device 7 and the lens system 24 as well as its optical axis 26 are arranged orthogonal to the plane of the PCB 21 like the LED's 5, 6.

The lens system 24 comprises a stack of lenses 27 stacked in the direction of the optical axis 26 thereby forming a so-called lens barrel, which is carried by the imaging/camera chip 23. Such a lens barrel-imaging chip-unit is well known in the prior art so that a detailed description is not needed here. The stack of lenses/lens barrel 27 is arranged within and surrounded by an opaque protective ring/cover/foil 28, which, in this example, is made by 2K molding with the transparent first housing part 9. Outside the protective ring 28 the first housing part 9 is provided with a circular opening (through hole) 35 designed to receive the protective ring 28 and the stack of lenses 27. The protective ring 28 also may serve for centering and adjusting the lens system 24. For this the ring 28 comprises a shoulder 29 providing an axial stop and an annular surface 30 for centering the distal end of the lens stack 27. The lens system 24 is arranged in a centered manner above (when related to the incoming light) the imaging chip 23, such that the image provided by the lens system 24 is projected onto the imaging chip 24, where it is transferred into image data, which are computed and/or stored by the PCB in a well-known manner.

To protect and shield light sensitive functional units of the tip 1, in particular the imaging device 7 with the imaging chip 23 and the lens system 24, from disturbing light which incidents into the transparent material of the housing 8, for example, from the outside and/or by the LED's 5, 6, at least parts of inner surfaces of the housing 8 facing the cavity 22 are covered/coated with an opaque coating 31. Additionally, or alternatively the imaging chip 23 is also shielded by an opaque potting 31 filled into the cavity 22. Further, a space between the stack of lenses 27 and the protective ring 28 may be filled/casted with additional opaque potting 31.

The tip 1 further comprises a (cleaning) nozzle 32. As the nozzle 32 is located below (radial outside of) the first light emitting device 5—which means within the area to be illuminated—it is also made of a transparent plastic material. Further, the nozzle 32 is preferably attached to the first housing part 9 of the tip 1 by a transparent grout 34, such that also the grout 34 does not negatively affect illumination by the first LED 5. Alternatively, the nozzle 32 and the housing may be provided integrally. The transparent nozzle 32 is designed for rinsing the tip 1, in particular an outer surface 33 of the imaging device 7. Further, the transparent nozzle 32 may be designed for insufflating a gas and/or air into a body cavity to be examined. Finally, in case of arranging a nozzle separate to the housing as described above, the (first) outside surface 18 has to be provided by the nozzle 32, itself.

As further is shown in FIGS. 2 to 7, an actuating lever (so-called Albarran lever) 36 is pivoted in the first housing part 9 as it is known in duodenum endoscope tips according to the prior art. The Albarran lever 36 is located besides the opening 35 in the longitudinal direction on the same side of the first housing 9 and also coaxial to the working channel 134 such that in a fully pivoted orientation of the Alberran lever 36 as shown in FIG. 5 a surgical instrument being shifted through the working channel 134 is deflected by the Albarran lever into the same radial direction as the lens system 24 and substantially parallel to the optical axes 25 of the lens system 24. Further, it should be noted, that in FIGS. 2 to 7 the tip 1 is shown without the PCB 21, the LEDs 5, 6 and the imaging device 7. Finally, it should be noted that the Albarran lever 36 is made of an opaque (resin) material thereby avoiding light reflections especially in case the Albarran lever is in fully pivoted orientation.

The assembly of the endoscope tip 1 for a single use duodenum endoscope is described as follows:

To begin with, the PCB 21 already carrying the LED's 5, 6 and the imaging device 7 including the imaging/camera chip 23 and the lens barrel 24 is attached to the first housing part 9 at socket-like connecting portions representing the first and second light guiding sections 14, 15 preferably by a glue layer. In this mounting/connecting position, the lens barrel penetrates the through opening within the first housing part 9 to be uncovered to the outside wherein the opaque protective ring 28 forms a light blocking layer between the lens barrel 24 and the first housing part 9.

In a following step, the light transparent nozzle 32 is connected with the first housing part 9 thereby forming a further light guiding part/section of the light emitting path below the one LED 5, wherein an outer surface of the nozzle 32 provides the first outer light emitting outside surface 18 of the respective light emitting path.

After the second housing part 11 is fluid tightly connected to the first housing part 9 at the respective housing seats 10, 12, cavities inside the housing 8 are filled with the opaque material surrounding at least the lens barrel 24, the LED's 5, 6 (including the contact area (glue layer) between the LED's 5, 6 and the first housing part 9), as well as the socket-like first and second light guiding sections 14, 15, thereby blocking light transmission through the housing 8, except the first and second outside surfaces 18, 19 at the first housing part 9 (and the nozzle 32).

REFERENCE SIGNS

1 tip
2 longitudinal axis of tip
3 proximal end
4 distal end
5 first light emitting device
6 second light emitting device
7 imaging device
8 housing
9 first housing part
10 housing seat
11 second housing part
12 housing seat
13 connection part, connection section
14 first light guiding section/part
15 second light guiding section/part
16 first inside surface
17 second inside surface
18 first outside surface
19 second outside surface
20 transparent glue
21 printed circuit board (PCB)
22 cavity
23 imaging chip
24 focusing system, lens system
25 optical axis or LED
26 optical axis of lens system
27 stack of lenses
28 opaque protective ring
29 shoulder
30 annular surface
31 opaque coating
32 nozzle
33 outer surface of imaging device
34 transparent grout
35 circular opening
36 Albarran lever
100 endoscope
120 connector unit
130 endoscope handle
131 manipulators
133 endoscope shaft
134 working channel

What is claimed is:

1. A tip for an endoscope, the tip comprising:

a housing comprising a proximal end, a distal end, and a circumferential wall portion extending longitudinally between the proximal end and the distal end, the housing further comprising a first housing part and a second housing part sealingly affixed to each other at a longitudinal seam, the first housing part comprised of a plastic material and comprising a light guiding section comprising a light entrance surface spaced apart from a light exit surface that is larger than the light entrance surface, a distance between the light entrance surface and the light exit surface filled by the plastic material and being greater than a thickness of the circumferential wall portion surrounding the light guiding section, the light entrance surface being part of an inside surface of the housing and the light exit surface being part of an outside surface of the housing, the outside surface being exposed to a patient during use;

a planar printed circuit board having a planar surface facing the circumferential wall portion;

a light emitting device mounted on the planar printed circuit board, the light emitting device comprising a light emission axis traversing the light entrance surface and the light exit surface; and an imaging device mounted on the planar printed circuit board and comprising an optical axis, the optical axis and the light emission axis traversing the planar printed circuit board at longitudinally apart locations and traversing the circumferential wall portion at longitudinally apart locations;

the housing enclosing the planar printed circuit board, the light emitting device and the imaging device.

2. The tip of claim 1, wherein the light emitting device comprises an LED.

3. The tip of claim 1, wherein the imaging device is arranged on and/or connected to the printed circuit board, wherein the printed circuit board is oriented substantially parallel to a longitudinal axis of the tip extending from a distal tip end to a proximal tip end.

4. The tip of claim 3, wherein the printed circuit board is oriented at an angle $\alpha$ of 4° to 10° to the longitudinal axis.

5. The tip of claim 4, wherein the angle $\alpha$ equals 6°.

6. The tip of claim 1, wherein the light emitting device is connected to the light entrance surface of the first housing part of the housing by a transparent adhesive without direct contact between the light emitting device and the housing.

7. The tip of claim 1, wherein the light exit surface of the light guiding section of the housing comprises a rough surface with a roughness RA of between 1 μm and 10 μm.

8. The tip of claim 7, wherein the rough surface has a roughness RA of 2.5 μm.

9. The tip of claim 1, wherein the tip comprises an opaque polymeric Albarran lever, wherein the imaging device comprises an imaging chip disposed on the printed circuit board and a lens system configured to provide an image onto the imaging chip, wherein the first housing part comprises an opening proximal of the light guiding section, and wherein the opening surrounds the lens system.

10. The tip of claim 9, comprising an opaque layer provided to shield disturbing light entering the housing, wherein the opaque layer shields the imaging chip and the lens system.

11. The tip of claim 9, wherein the lens system is surrounded by an opaque protective ring.

12. The tip of claim 1, wherein the plastic material of the first housing part is transparent, wherein the imaging device comprises an imaging chip disposed on the printed circuit board and a lens system configured to provide an image onto the imaging chip, wherein the first housing part comprises an opening proximal of the light guiding section and surrounding the lens system, wherein the first housing part further comprises an opaque protective ring, and wherein the opaque protective ring and the first housing part comprise one molded piece.

13. The tip of claim 1, wherein the light emission axis is substantially parallel to the optical axis of the imaging device.

14. The tip of claim 1, wherein the tip further comprises a transparent nozzle for rinsing an outer surface of the tip and/or for insufflating a gas and/or air.

15. The tip of claim 14, wherein the transparent nozzle is attached to the tip by a transparent grout.

16. The tip of claim 1, wherein the imaging device comprises an imaging chip and a lens system configured to provide an image onto the imaging chip, wherein the circumferential wall portion comprises a cavity surrounding the lens system.

17. The tip of claim 1, further comprising a second light emitting device mounted on the planar printed circuit board, wherein the imaging device is mounted on the planar printed circuit board longitudinally between the light emitting device and the second light emitting device.

18. The tip of claim 17, further comprising a second light guiding section comprising a second light entrance surface spaced apart from a second light exit surface that is larger than the second light entrance surface, a distance between the second light entrance surface and the second light exit surface filled by the plastic material and being greater than a thickness of the circumferential wall portion surrounding the second light guiding section.

19. The tip of claim 1, further comprising a second light emitting device, the first housing part further comprising a second light guiding section, wherein the imaging device is mounted on the planar printed circuit board longitudinally between the first light guiding section and the second light guiding section, wherein the second light guiding section comprises a second light entrance surface spaced apart from a second light exit surface that is larger than the second light entrance surface, a distance between the second light entrance surface and the second light exit surface filled by the plastic material and being greater than a thickness of the circumferential wall portion surrounding the second light guiding section.

20. An endoscope comprising:
- an endoscope shaft adapted to be inserted into a patient; and
- the tip of claim 1, the tip provided at a distal end of the endoscope shaft.

21. A method for manufacturing the tip of claim 1, the method comprising:
- inserting the planar printed circuit board within the housing, the imaging device being connected to the planar printed circuit board;
- connecting and/or attaching the light emitting device to the light guiding section of the housing with a transparent adhesive; and
- encapsulating the planar printed circuit board, the light emitting device and the imaging device in a fluid tight manner in the housing.

* * * * *